United States Patent [19]

Lee et al.

[11] Patent Number: 5,605,884
[45] Date of Patent: Feb. 25, 1997

[54] FACTOR VIII FORMULATIONS IN HIGH IONIC STRENGTH MEDIA

[75] Inventors: Ted C. K. Lee, Lansdale; Michael E. Hrinda, Gwynedd Valley, both of Pa.

[73] Assignee: Rhone-Poulenc Rorer Pharmaceuticals Inc., Collegeville, Pa.

[21] Appl. No.: 364,837

[22] Filed: Dec. 27, 1994

Related U.S. Application Data

[63] Continuation of Ser. No. 76,495, Jun. 14, 1993, abandoned, which is a continuation of Ser. No. 875,558, Apr. 27, 1992, abandoned, which is a continuation of Ser. No. 325,634, Mar. 20, 1989, abandoned, which is a continuation-in-part of Ser. No. 114,314, Oct. 29, 1987, abandoned.

[51] Int. Cl.⁶ .......................... A61K 38/36; A61K 38/37; C07K 14/745; C07K 14/755
[52] U.S. Cl. .............................. 514/8; 530/383; 930/100; 435/69.6
[58] Field of Search .................... 514/2, 8, 12, 21; 530/383; 930/100; 435/69.6

[56] References Cited

U.S. PATENT DOCUMENTS

| | | | |
|---|---|---|---|
| Re. 32,011 | 10/1985 | Zimmerman | 530/383 |
| 4,089,944 | 5/1978 | Thomas | 424/101 |
| 4,562,072 | 12/1985 | Heimburger et al. | 424/101 |
| 4,578,218 | 3/1986 | Saundry et al. | 530/383 |
| 4,597,966 | 7/1986 | Zolton et al. | 484/85.8 |
| 4,623,717 | 11/1986 | Fernandes et al. | 530/380 |
| 4,758,657 | 7/1988 | Farb | 530/383 |
| 4,877,608 | 10/1989 | Lee et al. | 424/85.8 |

OTHER PUBLICATIONS

Larsen et al. (1973) Arch Pharm Chemi. Sci. Ed. 1, 41–53.

Armour Pharmaceutical Corp. "Full Disclosure: Antihemophilic Factor (Human, Monoclate, Factor VIII:C, Heat-Treated".

*Primary Examiner*—Dian C. Jacobson
*Attorney, Agent, or Firm*—Raymond S. Parker, III; Rosanne Goodman; Martin F. Savitzky

[57] ABSTRACT

Stable, highly purified Factor VIII protein formulations are provided in high ionic strength media which comprises: sodium chloride, potassium chloride or mixtures thereof; calcium chloride; and histidine as the buffering agent.

6 Claims, No Drawings

FACTOR VIII FORMULATIONS IN HIGH IONIC STRENGTH MEDIA

This is a continuation of application Ser. No. 08/076,495 filed on Jun. 14, 1993, now abandoned which is a Continuation application of U.S. Ser. No. 07/875,558, filed on Apr. 27, 1992, now abandoned, which is a Continuation application of U.S. Ser. No. 07/325,634, filed on Mar. 20, 1989, now abandoned, which is a continuation-in-part application of U.S. Ser. No. 07/114,314, filed Oct. 29, 1987, now abandoned.

BACKGROUND OF THE INVENTION

1. Field of the Invention

This invention relates to stable Factor VIII formulations. More particularly, high purity Factor VIII protein is formulated in high ionic strength media for administration to patients suffering from hemophilia type A.

Antihemophilic factor or Factor VIII procoagulation activity protein (hereinafter Factor VIII) functions to correct the clotting defect in hemophilia type A plasma. Accordingly, Factor VIII preparations are extensively used for the purpose of supplying Factor VIII to hemophilic patients.

2. Description of the Prior Art

An important concern associated with the use of Factor VIII and other therapeutic agents derived from biological sources is the transmission of diseases, especially viral diseases. Prevalent viral contaminants include hepatitis B virus (HBV), non-A, non-B hepatitis virus (NANBV), and HTLV III/LAV/HIV which cause AIDS. In order to ensure that products produced from biological sources are virus-safe, various methodologies have been proposed for virus inactivation. However, most plasma protein preparations are unstable and require special care to prevent denaturation, alteration and loss of activity during the virus inactivation process. One approach to prevent denaturation and other alteration of plasma proteins utilizes additives during the pasteurization process. Representative examples follow.

U.S. Pat. No. 4,440,679 (Fernandes et al.) describes a method wherein therapeutically active proteins are pasteurized by mixing the protein composition with a pasteurization-stabilizing amount of a polyol prior to pasteurization.

U.S. Pat. No. 4,297,344 (Schwinn et al.) discloses a process for the stabilization against heat of the coagulation factors II, VIII, XIII, antithrombin III and plasminogen in aqueous solution, which comprises adding to the solution both an amino acid and one or more of a monosaccharide, an oligosaccharide or a sugar alcohol.

U.S. Pat. No. 4,585,654 (Landaburu et al.) pertains to a process of inactivating viruses in plasma protein solutions by heating the same in the presence of a polyol, a surface active agent and a chelating agent.

U.S. Pat. No. 4,446,134 (Naito et al.) is drawn to a virus-inactivating process in which Factor VIII is heated in an aqueous solution in the presence of one principal stabilizer of neutral amino acids, monosaccharides, oligosaccharides, and sugar alcohols and an auxiliary stabilizer of salts of hydrocarbon and hydroxyhydrocarbon carboxylic acids.

These processes aim at destroying the potential viral and bacterial infectivity of the preparations while substantially maintaining their desired biological activity. As such, they represent significant steps toward the provision of satisfactory plasma protein products to patients.

However, in order to be administrable, the plasma protein products need to be formulated with suitable compounds, lyophilized for storage and ready for reconstitution. Before formulating, the additives used during the pasteurization process are removed and their stabilizing/protecting effect is no longer present to prevent loss of activity. Applicants have encountered degradation problems with Factor VIII both during lyophilization and upon reconstitution with normal saline solution.

The inventors have extensively studied the problem of degradation in order to provide effective Factor VIII formulations for injection. A highly purified Factor VIII was used to study degradation occurring during lyophilization and reconstitution such as that produced by the teaching of U.S. Pat. No. 4,361,509 and U.S. Pat. Re. 32,011. The method there disclosed provides for about one thousand-fold purification of Factor VIII obtained from a commercial concentrate using an antibody column. The subsequent purification step by an Aminohexyl-Sepharose column chromatography further increases purity by 2 to 3-fold resulting in Factor VIII activity of about 2,300 units per mg of protein. Elution of Factor VIII from said Aminohexyl-Sepharose is accomplished by the use of a calcium chloride solution having a concentration of from 0.25 to 0.5M. This solution, while being eminently potent for the treatment of hemophilia type A, is less than satisfactory for two reasons: first, having such a high calcium chloride concentration, it is not suitable for injection to the patient; and second, upon lyophilization, a drastic loss of Factor VIII occurs.

To remedy the problems, an isotonic solution was prepared by dialyzing Factor VIII contained in said calcium chloride solution against 0.15M sodium chloride, 5 mM calcium chloride and 3 mM histidine at pH 6.8. Upon testing, a drastic loss of Factor VIII was again observed.

It has now been discovered that highly purified Factor VIII can be formulated with physiologically acceptable compounds for stabilization against loss of activity during storage in a liquid state, lyophilization, storage in the lyophilized state and reconstitution preceding administration to patients.

SUMMARY OF THE INVENTION

In accordance with the present invention, highly purified Factor VIII protein formulations are provided which are stable, and upon reconstitution, are ready for administration into patients. The formulations comprise Factor VIII having activity in the range of about 130 to about 11,000 units/mg of protein or higher as the active ingredient for therapeutic use and a high ionic strength media. The amount of Factor VIII present in a formulation is based on its activity and will vary accordingly. The high ionic strength media comprises in an aqueous solution:

(a) from about 0.4M to about 1.2M sodium chloride or potassium chloride or mixtures thereof and preferably about 1M sodium chloride;

(b) from about 2 mM to about 35 mM and preferably about 3.5 to 15 mM calcium chloride; and (c) from about 1 mM to about 50 mM and preferably about 2 to 10 mM histidine as buffer ion.

The pH of the media should be from about 6.0 to about 7.6 and preferably about 7.0.

Optionally, up to about 10% w/v of sugars, such as mannitol, sucrose and maltose, may be added to the formulations of the present invention for lyophilization.

The formulation is lyophilized and is reconstituted to comprise:

(a) from about 0.40 to about 1.2M sodium chloride or potassium chloride or mixtures thereof and preferably about 1M sodium chloride;

(b) from about 1.5 mM to about 35 mM and preferably about 3.5 to 15 mM calcium chloride; and (c) from about 1 mM to about 50 mM and preferably about 2 to 10 mM histidine as buffer ion.

The formulations containing 2 to 500 units of Factor VIII per ml of solution are essentially free of other proteins and have been found effective for the treatment of hemophilia.

DETAILED DESCRIPTION OF THE INVENTION

The invention will be described in detail in reference to highly purified Factor VIII procoagulant activity protein produced according to U.S. Pat. No. 4,361,509 and U.S. Pat. Re. 32,011. The method therein disclosed is capable of producing highly purified and concentrated Factor VIII which is effective in the treatment of hemophilia type A, having about 130 to 11,000 units of Factor VIII procoagulant activity per mg of protein. However, the product as obtained by the process is unstable during lyophilization and upon reconstitution. Furthermore, the high calcium ion solution containing the factor is undesirable for administration to the patients. The following examples and tests will further illustrate the invention.

EXAMPLE 1

The rate of Factor VIII degradation under isotonic conditions was studied. Factor VIII, obtained by the process of U.S. Pat. No. 4,361,509, in buffered 500 mM calcium chloride solution was dialyzed against 1M sodium chloride, 0.035M calcium chloride and 3 mM histidine at pH 6.8, for salt exchange, and then was lyophilized. Reconstitution of the lyophilized material was made to 0.167M sodium chloride, 5.8 mM calcium chloride, and 3 mM histidine by adding a 6-fold volume of sterile water, at pH 6.8, over the pre-lyophilization volume. The time dependent decay of Factor VIII activity was determined by a two stage assay method which is essentially the same as the methods described by Newman, J., Johnson A. J., Karpatkin, S. and Puszkin, S. (1971), Br. J. Haemotol. 21, pp. 1–20. The results are shown in Table I.

TABLE I

Time Dependent Decay of Factor VIII Activity Under Isotonic Conditions

| Time (Minutes) | Factor VIII Activity (Total Unit) | Loss of Factor VIII Activity % Decay |
| --- | --- | --- |
| 0 (At reconstitution) | 21 | 0 |
| 15 | 17 | 18 |
| 30 | 14 | 32 |
| 60 | 10 | 52 |

It is to be noted that, at the time of reconstitution, decay is 0% since degradation is time dependent; as time passes, degradation increases at a rapid pace.

EXAMPLE 2

High purity Factor VIII, having about 2,100 U/mg of protein activity, was prepared from cryoprecipitate of plasma obtained from Plasma Alliance (a division of Rorer Pharmaceutical Corporation) and prepared by the monoclonal antibody column procedure of Fulcher and Zimmerman (Proc. Natl. Acad. Sci. USA, 79, 1648 (1982) which essentially corresponds to the process taught in U.S. Pat. No. 4,361,509).

A set of formulations were made, by dissolving the ingredients in sterile water using standard laboratory technique, containing: 30 U/ml of Factor VIII; 3 mM histidine; and NaCl and $CaCl_2$ in amounts shown in Table II. The samples were assayed by the two stage method referred to in Example 1.

TABLE II

| NaCl M | $CaCl_2$ M | Factor VIII Activity % Recovery |
| --- | --- | --- |
| 1.2 | 0.005 | 100 |
| 1.0 | 0.005 | 100 |
| 0.70 | 0.005 | 91 |
| 0.40 | 0.005 | 70 |
| 0.15 | 0.005 | 0 |
| 0.05 | 0.005 | 0 |
| 0.01 | 0.005 | 0 |

It is apparent from Table II, that while $CaCl_2$ concentration is constant, the amount of Factor VIII recovery is controlled by the concentration of NaCl: below 0.40M NaCl, which is close to the lower limit of NaCl presence according to the invention, recovery is not sufficient; 100% recovery of Factor VIII is achieved at about 1.0M NaCl concentration, and such recovery is maintained at 1.2M NaCl. Increasing NaCl concentrations beyond 1.2M is not desirable in injectable formulations.

EXAMPLE 3

A set of formulations containing: 20 U/ml of Factor VIII and concentrations of NaCl shown in Table III were prepared and tested for Factor VIII recovery as in Example 1.

TABLE III

| NaCl % w/v | Factor VIII Activity % Recovery |
| --- | --- |
| 6.0 | 37 |
| 3.0 | 19 |
| 1.0 | 10 |
| 0.7 | 0 |

Table III shows that the presence of NaCl alone does not result in adequate recovery levels of Factor VIII.

The presence of large amounts of $CaCl_2$ do maintain adequate recovery levels of Factor VIII, as shown in Examples 4 and 5 and Tables IV and V. However, solutions containing such large amounts of $CaCl_2$ are undesirable for injection to patients.

EXAMPLE 4

A set of formulations containing: 41.8 U/ml of Factor VIII, 0.15M NaCl, 5 mM histidine and concentrations of $CaCl_2$ shown in Table IV were prepared and tested for Factor VIII recovery at reconstitution as in Example 1.

TABLE IV

Effect of CaCl₂ Concentration on Factor VIII Activity

| mM (CaCl₂) | Factor VIII Activity at Reconstitution U/ml | Percent |
| --- | --- | --- |
| 500 | 41.8 | 100 |
| 50 | 20.9 | 50 |
| 5 | 18.0 | 43 |

EXAMPLE 5

A set of formulations containing: 39.5 U/ml of Factor VIII, 0.15M NaCl, 5 mM histidine and concentrations of CaCl₂ shown in Table V were prepared and tested for Factor VIII recovery four (4) days after formulation as in Example 1.

TABLE V

Effect of CaCl₂ Concentration on Factor VIII Activity

| mM (CaCl₂) | Factor VIII Activity 4 days after Formulation U/ml | Percent |
| --- | --- | --- |
| 500 | 39.5 | 100 |
| 50 | 25.5 | 64 |
| 5 | 9.5 | 24 |

The following examples will further illustrate the result obtained by the present invention.

EXAMPLE 6

Factor VIII (43 U/ml), prepared by the process of U.S. Pat. No. 4,361,509, was placed in 1M sodium chloride, 5 mM calcium chloride, 3 mM histidine, at pH 7.0, and lyophilized. Reconstitution was made with 2.2 fold volume of water over the pre-lyophilization volume of Factor VIII. The reconstituted solution contained: 0.45M sodium chloride, 2.3 mM calcium chloride and 1.4 mM histidine. The recovery of Factor VIII was measured by the two stage assay method referred to in Example 1. The results are shown in Table VI.

TABLE VI

| Time (Minutes) | Factor VIII Activity U/ml |
| --- | --- |
| 0 | 20.0 |
| 20 | 19.5 |
| 45 | 19.7 |
| 60 | 19.5 |
| 120 | 19.5 |
| 150 | 19.4 |
| 180 | 19.3 |
| 210 | 19.2 |

EXAMPLE 7

Preparation of Solution of Cryoprecipitate

The starting material used for the preparation of Factor VIII was cryoprecipitate of human plasma. Each kg of cryoprecipitate was placed in 1.4 kg of cold pyrogen-free (PF) water. 60 ml each of 12% w/v glycine and 16% w/v sodium chloride was added to the mixture. The mixture was placed in a 37° C. water bath to dissolve most of the cryoprecipitate and agitated to extract the Factor VIII into the solution. The pH of the mixture was titrated from 7.45 to 6.95 with 30 ml of 1N acetic acid. 65 g of Rehsorptar (2% w/v aluminum hydroxide gel, Armour Pharmaceutical Company, Kankakee, Ill.) were added to the mixture and mixed for 20 minutes to absorb vitamin K-dependent clotting factors. The mixture was centrifuged at 3,000 xg for 20 minutes and the supernatant was collected. 14 ml of 1.5M sodium citrate were added to the supernatant. The pH of the mixture was 7.40. The mixture was treated with Rehsorptar once again and centrifuged as above. The resultant protein solution was stored at −40° C. until used.

Isolation of Factor VIII by Monoclonal Anti-von Willebrand Factor Antibody Column Chromatography The affinity column matrix was prepared by conjugation of monoclonal anti-von Willebrand Factor antibody to Sepharose gel (4 g of antibody per 1 g of Sepharose gel). Thawed cryoprecipitate solution, 4.8 l (18,280 units of Factor VIII) were applied to a 1.3 l (9×21 cm) size of the antibody column, which was equilibrated with Factor VIII buffer (0.15M sodium chloride, 0.1M lysine hydrochloride, 0.02M histidine, pH 6.8). The flow rate of the loading was 15 ml per minute. The column was then washed with 3 column volumes of the Factor VIII buffer. A total of 4,340 units was not bound to the column. The Factor VIII was eluted from the antibody column with 0.5M calcium chloride in the Factor VIII buffer (flow rate: 21 ml/minute). The recovered Factor VIII activity was 7,610 units in 0.68 l of the column eluate.

Concentration, Formulation, Lyophilization and Reconstitution

The recovered Factor VIII was concentrated in an Amicon Hollow Fiber System (Type HIX 50-20, 2.5 cm×20 cm long). The concentrated Factor VIII, 50 g (56 U/ml, 2,800 units), was dialyzed at 4° C. overnight against a formulation buffer which consisted of 1M sodium chloride, 5 mM calcium chloride, 3 mM histidine, pH 7.0, with 2 changes. The dialyzed material, 46 U/ml, was lyophilized. The reconstitution of the lyophilized material was made to 0.45M sodium chloride, 2.3 mM calcium chloride, 1.4 mM histidine, pH 7.0 by addition of 2.2 volumes of water for injection (WFI) over the pre-lyophilization volume. The reconstituted material was remarkably stable over a period of 3 hours and the recovery of the Factor VIII activity was about 91%. The assay values (18 to 20 U/ml) were essentially the same, within experimental error, as shown in Table VII.

TABLE VII

| Time (Minutes) After Reconstitution | 9 | 21 | 33 | 46 | 68 | 95 | 125 | 191 |
| --- | --- | --- | --- | --- | --- | --- | --- | --- |
| Activity (U/ml) | 18 | 19 | 20 | 19 | 19 | 20 | 19 | 18 |

EXAMPLE 8

The solution prepared from 3.113 kg of cryoprecipitate of human plasma (18,297 units of Factor VIII) was applied to an affinity column (13.7 cm×22.0 cm, 3.24 l) of monoclonal anti-von Willebrand antibody gel matrix, which was prepared by conjugation of 1.2 g of the antibody per liter of Sepharose gel. The column was then washed with 3 column volumes of the Factor VIII buffer of Example 7. 19% (3,537 units) of the Factor VIII were not bound to the column. The column was eluted with 0.25M calcium chloride in the Factor VIII buffer. The Factor VIII activity containing portion, 3.556 kg (9,880 units), was collected. The eluted Factor VIII was applied on an Aminohexyl-Sepharose column (2.5 cm×5.6 cm, Pharmacia) immediately after a five-fold in-line dilution with the AH-Sepharose equilibration buffer (20 mM histidine, 100 mM lysine hydrochloride, pH 6.8). The flow rate was 12 ml per minute.

There was no detectable Factor VIII activity in the solution that passed through the AH-Sepharose column. The column was washed with 209 g of 50 mM calcium chloride in the AH-Sepharose equilibration buffer. A small amount of Factor VIII activity (165 units, 1.7%) was detected in the wash buffer solution collected. The Factor VIII was then eluted from the column with 500 mM calcium chloride in the AH-Sepharose equilibration buffer. The peak fraction of the elution profile contained 6,890 units of Factor VIII in 26.5 g. The eluted Factor VIII was dialyzed overnight at 4° C. against the formulation buffer solution composed of 1M sodium chloride, 5 mM calcium chloride, 3 mM histidine, 2% mannitol, pH 7.0. The dialyzed Factor VIII had 266 U/ml (23 g).

EXAMPLE 9

1 kg frozen human plasma cryoprecipitate was placed in a solution of 2.8 kg of 0.055M glycine and 0.038M sodium chloride. The mixture was placed in a 37° C. water bath and agitated under laminar flow of air to dissolve the cryoprecipitate. 0.1N acetic acid was added dropwise to the suspension to bring the pH to 6.90±0.1. 100 g of Rehsorptar was added to the mixture, and agitated for 15 to 20 minutes at 35° to 37° C. The suspension was centrifuged at 4,000 x g at room temperature for 15 minutes and the supernatant was collected. The Rehsorptar treatment was repeated. The supernatant (3.8 kg) was mixed with 0.94 kg of 5M sodium chloride solution to make the mixture 1M in sodium chloride. The mixture had 7.6 units Factor VIII activity per ml (35,811 units total). 4.6 kg of the mixture (35,250 units) were loaded on a 7.1 l (25×14.5 cm) size monoclonal anti von-Willebrand antibody column (1.2 g of the antibody conjugated per 1 of sepharose) at room temperature with a flow rate of 14 ml per minute. The column was washed with 11.6 kg of 1M sodium chloride in the Factor VIII buffer solution of Example 7. The non-bound Factor VIII activity was 5,950 units. The adsorbed Factor VIII was eluted with 0.25M calcium chloride in the Factor VIII buffer. A total of 20,090 units of Factor VIII was collected in 10.1 kg of eluate. The eluted Factor VIII was chromatographed through an Aminohexyl-Sepharose column (5×3 cm) which was previously equilibrated with 0.02M histidine, 0.10M lysine hydrochloride, pH 6.8. The Factor VIII was applied on the AH-Sepharose column at 4° C. after 5-fold dilution with the AH-Sepharose equilibration buffer. The flow rate was 44 ml per minute. All of the Factor VIII activity was bound to the column. The column was washed with 420 g of 0.05M calcium chloride in the above referred to equilibration buffer. 4,349 units of Factor VIII were washed off. The Factor VIII was then eluted from the column with 0.50M calcium chloride in the equilibration buffer. The Factor VIII activity (12,538 units) was collected in 90.81 g of the eluate. The isolated Factor VIII was dialyzed overnight at 4° C. against 1M sodium chloride, 3 mM histidine, 5 mM calcium chloride, pH 7.0, with 2 changes. 12,621 units of Factor VIII were recovered. The material was stored at 4° C. for several days. To a sample of Factor VIII solution, powdered mannitol was added to make 2% w/v in mannitol (83 units/ml). The mixture was lyophilized and reconstituted and 72 units per ml were recovered. To another sample of Factor VIII solution, powdered maltose was added to make 2% w/v in maltose (96 units/ml). The mixture was lyophilized and reconstituted and 94 units per ml were recovered.

It should be understood by those skilled in the art that various modifications may be made in the present invention without departing from the spirit and scope thereof as described in the specification and defined in the appended claims.

What is claimed is:

1. A stable Factor VIII formulation in an aqueous solution for the treatment of hemophilia type A consisting essentially of:

a therapeutically effective amount of Factor VIII having an activity of at least 130 U/mg of protein;

from about 0.40M to about 1.2M sodium chloride, potassium chloride, or mixtures thereof;

from about 1.5 mM to about 40 mM calcium chloride; and from about 1 mM to about 50 mM histidine;

said formulation having a pH of from about 6.0 to about 7.6.

2. The formulation of claim 1 wherein said Factor VIII has a concentration of from about 2 to 500 units per ml of solution.

3. A stable Factor VIII formulation in an aqueous solution for the treatment of hemophilia type A consisting essentially of:

a therapeutically effective amount of Factor VIII having an activity of about 130 U/mg to about 11,000 U/mg of protein;

from about 0.40M to about 1.2M sodium chloride, potassium chloride, or mixtures thereof;

from about 1.5 mM to about 40 mM calcium chloride; and from about 1 mM to about 50 mM histidine;

said formulation having a pH of from about 6.0 to about 7.6.

4. A stable Factor VIII formulation in an aqueous solution for the treatment of hemophilia type A consisting essentially of:

from about 2 to about 500 units of Factor VIII per ml of solution, said Factor VIII having an activity of least 130 U/mg of protein;

about 1M sodium chloride, potassium chloride, or mixtures thereof;

from about 3.5 mM to about 15 mM calcium chloride; and from about 2 mM to about 10 mM histidine;

said aqueous solution having a pH of from about 6.0 to about 7.6.

5. A stable Factor VIII formulation in an aqueous solution for the treatment of hemophilia type A consisting essentially of:

a therapeutically effective amount of Factor VIII having an activity of about 130 U/mg to about 11,000 U/mg of protein;

from about 0.40M to about 1.2M sodium chloride, potassium chloride, or mixtures thereof;

from about 1.5 mM to about 40 mM calcium chloride;

from about 1 mM to about 50 mM histidine;

said formulation having a pH of from about 6.0 to about 7.6; and up to 10% w/v of a sugar selected from the group consisting of mannitol, sucrose and maltose.

6. The formulation of claim 5 wherein said Factor VIII has a concentration of from about 2 to 500 units per ml of solution.

* * * * *